United States Patent [19]

Felix et al.

[11] Patent Number: 5,417,664
[45] Date of Patent: May 23, 1995

[54] REFLUX CONTAINMENT DEVICE FOR NASOGASTRIC TUBES

[75] Inventors: Augustus Felix, Providence; Robert Sakal, Briston, both of R.I.; Jacqueline Lipton, North Chelmsford, Mass.

[73] Assignee: C. R. Bard, Inc., Murray Hill, N.J.

[21] Appl. No.: 186,904

[22] Filed: Jan. 26, 1994

Related U.S. Application Data

[63] Continuation of Ser. No. 142,701, Oct. 25, 1993, abandoned.

[51] Int. Cl.⁶ .............................................. A61M 1/00
[52] U.S. Cl. ...................................... 604/129; 604/45; 604/247; 604/256
[58] Field of Search ................... 604/27, 45, 118, 128, 604/129, 247, 270, 284, 902, 256, 280

[56] References Cited

U.S. PATENT DOCUMENTS

| | | |
|---|---|---|
| 2,568,566 | 9/1951 | Sokolik . |
| 2,930,378 | 3/1960 | Buyers . |
| 3,044,466 | 7/1962 | Henderson . |
| 3,114,373 | 12/1963 | Andersen . |
| 3,419,009 | 12/1968 | Ericson . |
| 3,429,314 | 2/1969 | Ericson . |
| 3,730,209 | 5/1973 | Binard et al. . |
| 3,861,394 | 1/1975 | Villari . |
| 4,106,509 | 8/1978 | McWhorter . |
| 4,324,238 | 4/1982 | Genese et al. . |
| 4,508,533 | 4/1985 | Abramson . |
| 4,573,965 | 3/1986 | Russo ..................... 604/30 |
| 4,725,268 | 2/1988 | Ostensen et al. . |
| 4,735,606 | 4/1988 | Davison . |
| 4,735,607 | 4/1988 | Keith, Jr. ............. 604/129 |
| 4,743,243 | 5/1988 | Vaillancourt . |
| 4,813,931 | 3/1989 | Hauze . |
| 5,207,655 | 5/1993 | Sheridan . |
| 5,273,523 | 12/1993 | Suzuki et al. ......... 604/45 |

*Primary Examiner*—C. Fred Rosenbaum
*Assistant Examiner*—Mark Bockelman
*Attorney, Agent, or Firm*—Kane, Dalsimer, Sullivan, Kurucz, Levy, Eisele and Richard

[57] ABSTRACT

A double lumen nasogastric tube possesses a hydrophobic filter at the proximal end of the sump lumen for inhibiting reflux from exiting the sump lumen and contaminating the patient, clinician and nearby surroundings.

5 Claims, 3 Drawing Sheets

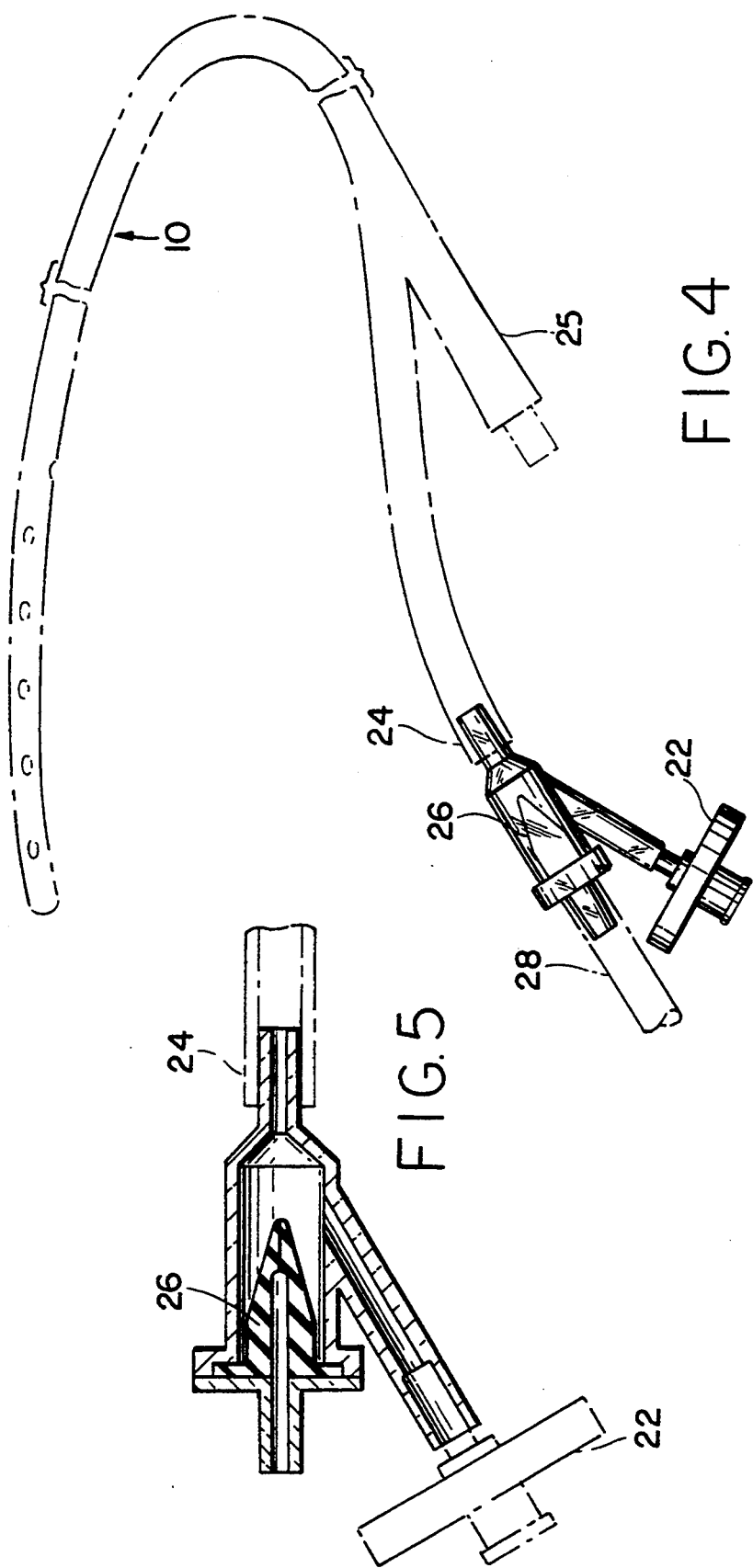

REFLUX CONTAINMENT DEVICE FOR NASOGASTRIC TUBES

REFERENCE TO RELATED APPLICATION

This application is a continuation of application Ser. No. 08/142,701 filed Oct. 25, 1993, now abandoned.

BACKGROUND OF THE INVENTION

The present invention relates generally to nasogastric tubes used, for example, to aspirate fluids from the gastrointestinal tract, or as feeding tubes for administering medicines or nutrients to a patient.

The primary purpose of a nasogastric tube is to aspirate fluid and air and decompress the contents of the stomach without damaging the gastric mucosa. In this regard, indwelling nasogastric tubes are used for clinical applications designed to remove accumulated fluids or blood from the stomach or gastrointestinal tract due to intestinal obstruction and consequent to decreased gastrointestinal function following abdominal surgery, bleeding ulcers or disease.

Nasogastric tubes are frequently placed in patients undergoing laparoscopic and open abdominal surgery to keep the stomach empty. In addition patients with intestinal obstruction and paralytic ulcers (temporary paralysis of the stomach/intestinal tract) may require a nasogastric tube to prevent progressive distension of the stomach/intestional tract. Progressive distension of the stomach/intestinal tract can lead to vomiting, shock, and visceral injury. In a severely ill patient, vomit may be aspirated into the respiratory tract and cause asphyxia and pneumonia.

The physician typically introduces the nasogastric tube which is conventionally a double lumen flexible plastic tube through one nostril, through the oropharynx and through the esophagus into the stomach for aspirating fluids or the duodenum for feeding. The distal end of the tube in the stomach includes several openings suction ports or openings for permitting the passage of gastric fluids. The proximal end of the tube exits the nostril, is pulled to the side of the patient's head and may be taped to the skin and is normally connected through a collector vessel to a suction source. Thus, stomach fluids are drawn through the openings in the distal end, through the tube into the collector vessel.

The nasogastric tube contemplated by the present invention is a double lumen sump tube of the type discussed above used to decompress the stomach in a manner well known in the art. The large lumen is used for suction drainage and irrigation and is connected to a suction source providing either intermittent or continuous suction. The smaller lumen vents the suction drainage lumen to the atmosphere through a perforation or opening in the distal end of the tube. With a dual lumen sump tube, the constant flow of atmospheric air moderates the amount of suction and flow from the stomach never stops, provided the suction openings do not become clogged and the sump lumen obstructed and filled with gastric fluids.

During normal suctioning operation of the nasogastric tube, a small amount of atmospheric air is drawn through the sump lumen into the stomach and suction lumen at the distal end. If there is fluid in the sump lumen due to reflux (i.e. stomach fluids backing up into the sump lumen), the required constant flow of incoming air is not provided. Thus, a non-functioning tube may actually be detrimental to the patient. As mentioned earlier, if air/gastric fluids are not removed, progressive distension of the stomach/intestinal tract can result in vomiting and other complications like pulmonary aspiration and asphyxiation. Accordingly, proper operation of the double lumen nasogastric tube depends on the continuous availability of atmospheric air to the suction openings at the distal end through the cooperation between the suction lumen and the sump lumen at the distal end.

A common problem encountered in using nasogastric tubes is the clogging or occlusion of the openings in the distal end leading into the suction lumen. The clogging may be the result of stomach debris, covering the openings or occlusion could be the result of the openings laying against the stomach or gastric mucosa. In either event, the air/gastric fluids cannot be suctioned.

In the event stomach pressure becomes greater than atmospheric pressure, gastric reflux can occur, causing stomach fluids to escape through the sump lumen. Unfortunately gastric reflux is a common problem with nasogastric tubes. Stomach fluids backing up the sump lumen and spilling onto the bed sheets, patient's clothing and even onto the patient is bothersome, a nuisance, and potentially dangerous because of the possible exposures to infectious body fluids and blood and contaminated laundry by doctors, nurses, clinicians and hospital staff. In this regard, studies have shown that the digestive tract is the main cause of aerobic gram-negative bacteria, the most frequent cause of ICU infections. Of course contaminated blood of a patient may cause other serious problems.

SUMMARY OF THE INVENTION

It is a principal object of the present invention to provide a double lumen nasogastric tube that has incorporated therein a gastric reflux containment device for effectively eliminating the undesirable consequences of gastric reflux.

A further object is to provide a nasogastric tube of the foregoing type that permits air to pass both in and out of the sump lumen, and, consequently, will not trap air inside the stomach.

Other objects and advantages will become apparent from the double lumen nasogastric tube of the present invention which has incorporated therein an acid resistant hydrophobic filter at the proximal end of the sump lumen. In the event positive pressure in the stomach forces stomach contents (reflux) up the sump lumen, the filter stops the reflux from exiting the proximal end of the lumen and spilling on the patient, attending hospital staff and nearby surroundings including the patient's clothes and bed sheets. In this manner, the filter also eliminates any risks and contamination associated with fluid and possible blood contact.

BRIEF DESCRIPTION OF THE DRAWINGS

FIG. 4 is an elevational view partly in phantom of another embodiment of nasogastric tube in which the filter is arranged in parallel with a one-way valve at the proximal end of the sump lumen;

FIG. 5 is an enlarged elevational view, partly in section of the valve and filter at the proximal end of the sump lumen, shown in phantom.

DETAILED DESCRIPTION OF THE INVENTION

Figure 1:
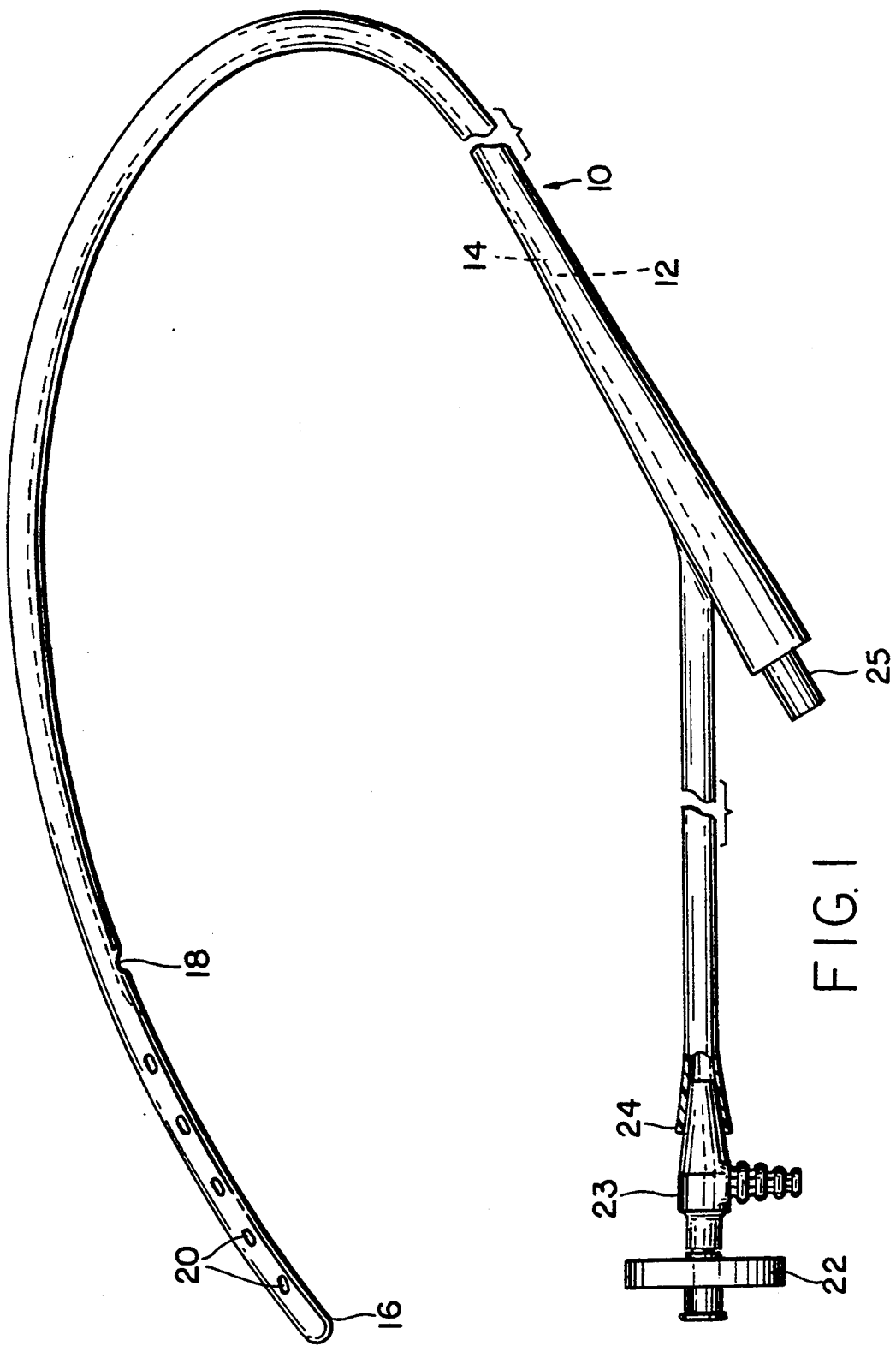
FIG. 1 is an elevational view of the double lumen nasogastric tube of the present invention.
Figure 2:
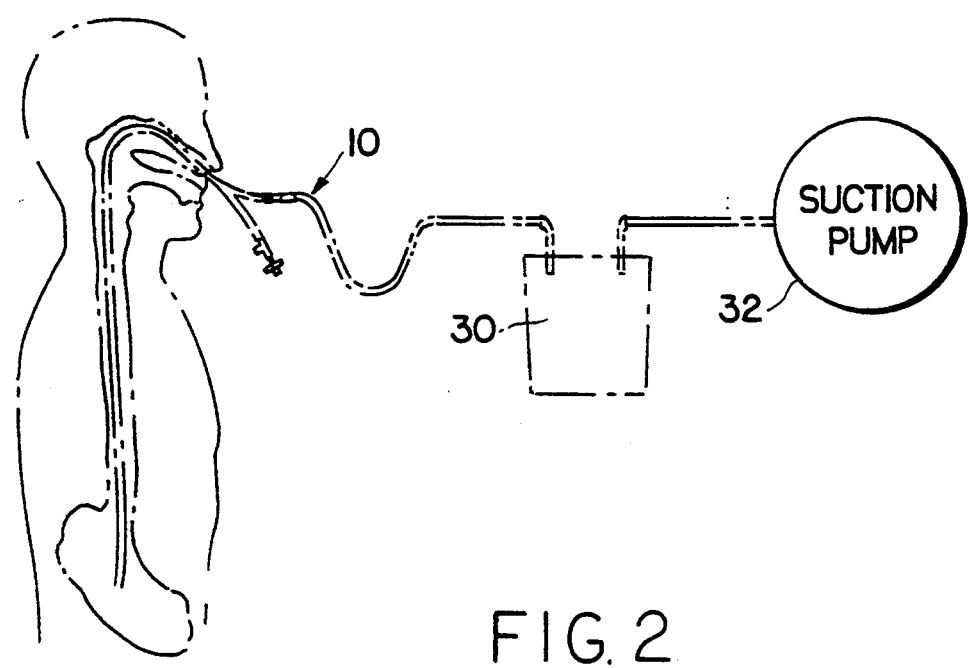
FIG. 2 is a schematic view showing the nasogastric tube connected to a patient, collector vessel and suction source.
Figure 3:
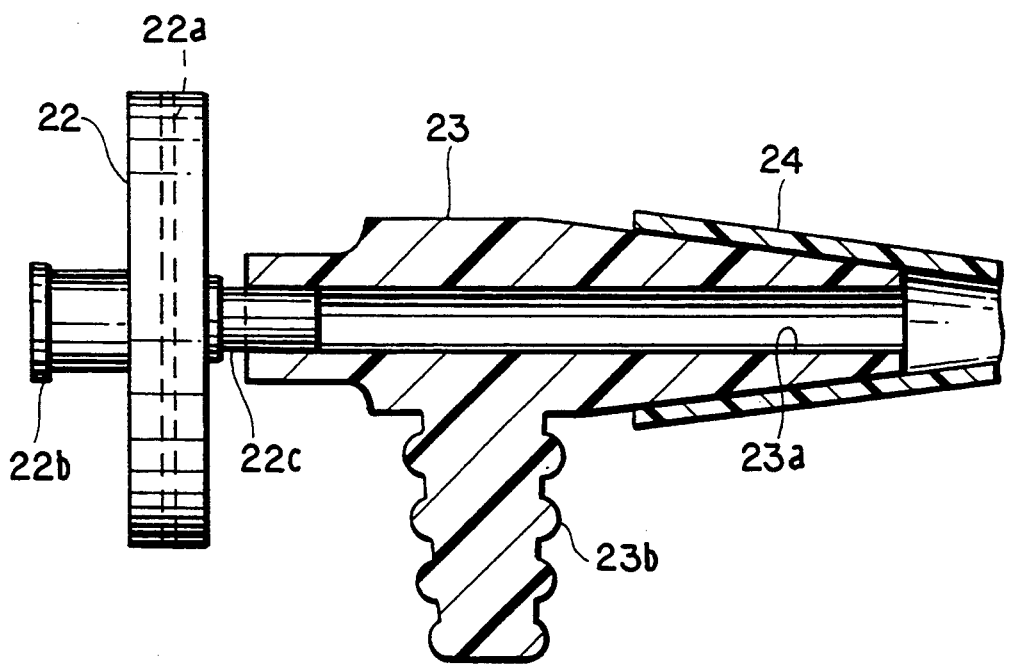
FIG. 3 is an enlarged elevational view partly in section, of the hydrophobic filter and adapter at the proximal end of the sump lumen, shown in phantom.

In the drawings, the nasogastric tube 10 of the present invention is fabricated from a dual lumen vinyl tube, with a large diameter lumen 12 and a small diameter lumen 14. The large lumen 14 is used as the main suction lumen while the smaller lumen 14 is used as a sump or vent lumen to irrigate air or liquid to the distal tip or end 16 of the tube through opening 18 in order to maintain the patency of the suction lumen 12.

The sump lumen 14 is normally left open to atmosphere because continuous air flow is necessary for the drainage procedure. In some cases, however, the openings 20 at the distal end 16 of the suction lumen 12 or the suction lumen 12 itself becomes occluded as previously explained. The ensuing volume and pressure build-up in the stomach will normally force the contents or reflux up and out of the sump lumen 14.

In accordance with a preferred embodiment of the invention a hydrophobic filter 22 having a hydrophobic filter medium 22a is placed at the proximal end 24 of the sump lumen 14. The hydrophobic filter 22 provides a means for continuous air entrainment through the vent lumen 14 but prevents the flow of gastric fluid beyond the inside surface of the filter medium 22a. The hydrophobicity and acid resistant properties of the filter medium 22a prevents the filter medium 22a from "wetting out" and becoming occluded which reduces filter efficiency. Air can be irrigated from the atmospheric side of the filter 22 to remove the blockage at the distal end of the tube and reestablish flow within the sump lumen 14. In this connection female Luer Lock 22b is conveniently adapted to receive the male Luer Lock of a syringe that may be conveniently deployed for introducing air through the filter medium 22a into sump lumen 14. In a successful application of the invention filter 22 possessed a filter medium 22a fabricated of PTFE (polytetrafluoroethylene) having 1 micron pore size and the desired hydrophobic and acid resistant properties and was obtained commercially under the name ACRODISC from its supplier Gelman Sciences of Ann Arbor, Mich. Male slip Luer 22c of filter 22 advantageously fits within the proximal end of adapter 23 the distal end of which fits within the proximal end 24 of sump lumen 14. The adapter 23 has a through bore 23a and a laterally extending plug 23b. Plug 23b serves the purpose of sealing the proximal end 25 of the suction lumen 12 during patient transport. This sealing action stops the contents of the stomach from backing-up the suction lumen 12 and contaminating the patient, clinician and the nearby surroundings.

In another embodiment a one-way duck bill valve 26 that opens inwardly is placed in parallel with the hydrophobic filter 22 in the sump lumen 14 at the proximal end 24. The one-way valve 26 allows the clinician to flush the sump lumen 14 with either air or liquid introduced through tubing 28 to reestablish patency of the sump lumen 14. The one-way action of the valve 26 allows liquid to be injected without spillage and assures the containment of the stomach contents during reflux.

The recognized procedure for applying the nasogastric tube 10 to a patient entails inserting a properly lubricated, measured and marked tube through the patient's nostril until it reaches the pharynx. Thereafter, the tube is advanced until the distal end 16 is in the stomach and this disposition is verified. The tube is then taped to the patient's nose. The proximal end 25 of the suction lumen 12 is connected to a collection vessel 30 and a suction pump 32 in the usual manner.

Upon actuation of the suction pump 32 for either intermittent or continuous operation, and assuming the pressure at the distal end 16 of the tube 10 is below atmospheric pressure, a sump action takes place. When this occurs, atmospheric air is drawn through filter 22 through the sump lumen 14 and opening 18 as the gastric fluids are withdrawn through openings 20 and suction lumen 12.

In the event, openings 20 and/or suction lumen 12 become occluded, the pressure at the distal end 16 of the tube 10 will ordinarily increase above atmospheric pressure. In this event, the gastric fluids will rise in sump lumen 14. The presence of filter 22 and its hydrophobic properties contains gastric reflux and prevents wetting of the filter, and, consequently, and tendency of the reflux emerging or spilling out the proximal end 24 of the sump lumen 14. Corrective action by the clinician will then be performed to remove the occlusion, reestablish patency of the sump lumen 14 and flow through the suction lumen 12.

Thus, the several aforenoted objects and advantages are most effectively attained. Although several somewhat preferred embodiments of the invention have been disclosed and described in detail herein, it should be understood that this invention is in no sense limited thereby and its scope is to be determined by that of the appended claims.

What is claimed is:

1. A nasogastric dual lumen tube having a distal end and a proximal end with the distal end being adapted for insertion through the nasal canal and esophagus into the stomach or small intestine of a patient, said dual lumen tube comprising a suction lumen having a distal end and a proximal end and sump lumen having a distal end and a proximal end, said suction lumen having at least one opening at its distal end and coupling means at its proximal end for attaching the suction lumen to a suction pump, said sump lumen being so constructed and arranged for continuous air entrapment for maintaining patency of the suction lumen and having at least one opening at its distal end and a gastric reflux containment device that prevents gastric reflux from discharging from the proximal end of the sump lumen incident to pressure at the distal end of the sump lumen increasing above atmospheric pressure as a result of occlusion of the opening in the suction lumen or of the suction lumen, the gastric reflux containment device including a filter at its proximal end for the passage of atmospheric air therethrough into the sump lumen and prevention of gastric reflux therethrough from the sump lumen, the filter having a distal surface and being hydrophobic and acid resistant and being so constructed and arranged and of such a nature to be free from wetting by gastric fluids and to prevent flow of gastric fluids beyond the distal surface of the filter, the filter being made from polytetrafluoroethylene having a pore size of about 1 micron.

2. The invention in accordance with claim 1 wherein an adapter is adapted to be interposed between the filter and proximal end of the sump lumen, the adapter having a through bore communicating with the filter and the sump lumen, the adapter having a lateral plug for sealing the proximal end of the suction lumen during patient transport.

3. The invention in accordance with claim 1 wherein a one-way valve is arranged in parallel with the filter at the proximal end of the sump lumen and being adapted to open inwardly into the sump lumen, the valve allowing fluids to be injection into the sump lumen while containing gastric fluids during reflux.

4. The invention in accordance with claim 3 wherein the valve is a duck bill valve.

5. A nasogastric dual lumen tube having a distal end and a proximal end with the distal end being adapted for insertion through the nasal canal and esophagus into the stomach or small intestine of a patient, said dual lumen tube comprising a suction lumen having a distal end and a proximal end and sump lumen having a distal end and a proximal end, said suction lumen having at least one opening at its distal end and coupling means at its proximal end for attaching the suction lumen to a suction pump, said sump lumen being so constructed and arranged for continuous air entrapment for maintaining patency of the suction lumen and having at least one opening at its distal end and a gastric reflux containment device that prevents gastric reflux from discharging from the proximal end of the sump lumen incident to pressure at the distal end of the sump lumen increasing above atmospheric pressure as a result of occlusion of the opening in the suction lumen or of the suction lumen, the gastric reflux containment device including a filter at its proximal end for the passage of atmospheric air therethrough into the sump lumen and prevention of gastric reflux therethrough from the sump lumen, the filter having a distal surface and being hydrophobic and acid resistant and being so constructed and arranged and of such a nature to be free from wetting by gastric fluids and to prevent flow of gastric fluids beyond the distal surface of the filter wherein an adapter being adapted to be interposed between the filter and proximal end of the sump lumen, the adapter having a through bore communicating with the filter and the sump lumen, the adapter having a lateral plug adapted to be removably attached to the proximal end of the suction lumen for sealing the proximal end of the suction lumen during patient transport.

* * * * *